US008450536B2

(12) United States Patent
White et al.

(10) Patent No.: US 8,450,536 B2
(45) Date of Patent: May 28, 2013

(54) METHODS OF HIGHER ALCOHOL SYNTHESIS (75) Inventors: Emily Bostwick White, Wheat Ridge, CO (US); Cherie Wilson, Lakewood, CO (US); Mark Berggren, Golden, CO (US); Robert M. Zubrin, Indian Hills, CO (US)

(73) Assignee: Pioneer Energy, Inc., Lakewood, CO (US)

( * ) Notice: Subject to any disclaimer, the term of this patent is extended or adjusted under 35 U.S.C. 154(b) by 588 days.

(21) Appl. No.: 12/504,913

(22) Filed: Jul. 17, 2009

(65) Prior Publication Data

US 2010/0088951 A1 Apr. 15, 2010

Related U.S. Application Data (60) Provisional application No. 61/081,578, filed on Jul. 17, 2008.

(51) Int. Cl.
| C07C 29/00 | (2006.01) |
| B01J 23/00 | (2006.01) |
| C07C 29/34 | (2006.01) |
| B01J 21/18 | (2006.01) |
| B01J 23/34 | (2006.01) |
| B01J 23/72 | (2006.01) |

(52) U.S. Cl.
CPC ............... *C07C 29/34* (2013.01); *B01J 21/18* (2013.01); *B01J 23/34* (2013.01); *B01J 23/72* (2013.01); *C07C 2523/04* (2013.01)
USPC ........... 568/905; 502/184; 502/324; 502/343; 502/346

(58) Field of Classification Search
CPC .................................. C07C 29/34; B01J 23/18
USPC .................. 568/905; 502/184, 324, 343, 346
See application file for complete search history.

(56) References Cited

U.S. PATENT DOCUMENTS

| 494,647 | A | 4/1893 | Preston |
| 2,595,979 | A | 5/1952 | Pevere et al. |
| 2,623,596 | A | 12/1952 | Whorton et al. |
| 3,051,235 | A | 8/1962 | Banks |
| 3,084,919 | A | 4/1963 | Slater |
| 3,193,006 | A | 7/1965 | Lewis |
| 3,327,782 | A | 6/1967 | Hujsak |
| 3,480,082 | A | 11/1969 | Gilliland |
| 3,725,246 | A | 4/1973 | Kmercak et al. |
| 3,918,263 | A | 11/1975 | Swingle |
| 4,024,912 | A | 5/1977 | Hamrick et al. |
| 4,114,688 | A | 9/1978 | Terry |
| 4,141,417 | A | 2/1979 | Schora et al. |
| 4,183,405 | A | 1/1980 | Magnie |
| 4,186,800 | A | 2/1980 | Allen |
| 4,239,499 | A | 12/1980 | Pfefferle |
| 4,241,790 | A | 12/1980 | Magnie |
| 4,250,230 | A | 2/1981 | Terry |
| 4,261,420 | A | 4/1981 | Hitzman |
| 4,299,286 | A | 11/1981 | Alston |
| 4,372,386 | A | 2/1983 | Rhoades et al. |
| 4,444,257 | A | 4/1984 | Stine |
| 4,446,919 | A | 5/1984 | Hitzman |
| 4,508,064 | A | 4/1985 | Watanabe |
| 4,597,441 | A | 7/1986 | Ware et al. |
| 4,622,275 | A | 11/1986 | Noguchi et al. |
| 4,657,887 | A * | 4/1987 | Hardman et al. ............ 502/303 |
| 4,659,634 | A | 4/1987 | Struthers |
| 4,687,491 | A | 8/1987 | Latty |
| 4,691,771 | A | 9/1987 | Ware et al. |
| 4,706,751 | A | 11/1987 | Gondouin |
| 5,033,940 | A | 7/1991 | Baumann |
| 5,059,404 | A | 10/1991 | Mansour et al. |
| 5,069,685 | A | 12/1991 | Bissett et al. |
| 5,079,103 | A | 1/1992 | Schramm |
| 5,089,532 | A * | 2/1992 | King et al. .................... 518/713 |
| 5,105,887 | A | 4/1992 | Hewgill et al. |
| 5,128,307 | A * | 7/1992 | Wanjek et al. ................ 502/342 |
| 5,133,406 | A | 7/1992 | Puri |
| 5,145,003 | A | 9/1992 | Duerksen |
| 5,458,857 | A | 10/1995 | Collins et al. |
| 5,590,518 | A | 1/1997 | Janes |
| 5,674,053 | A | 10/1997 | Paul et al. |
| 5,687,559 | A | 11/1997 | Sato |
| 5,691,268 | A * | 11/1997 | Koveal et al. ................. 502/345 |
| 5,755,089 | A | 5/1998 | Vanselow |
| 5,769,165 | A | 6/1998 | Bross et al. |
| 5,769,610 | A | 6/1998 | Paul et al. |
| 6,016,867 | A | 1/2000 | Gregoli et al. |
| 6,016,868 | A | 1/2000 | Gregoli et al. |

(Continued)

FOREIGN PATENT DOCUMENTS

| CA | 2647825 | 10/2007 |
| WO | WO 03/018958 | 3/2003 |
| WO | WO 2005/007776 | 1/2005 |
| WO | WO 2007/117933 | 10/2007 |
| WO | WO 2008/074980 | 6/2008 |

OTHER PUBLICATIONS

OTHER PUBLICATIONS

"Economies of Scale" Encyclopedia of Business, 2nd ed. Available Website: http://www.referenceforbusiness.com/encyclopedia/Eco-Ent/Economies-of-Scale.html Accessed on May 25, 2010.
"Countercurrent exchange" From Wikipedia, the free encyclopedia, retrieved May 20, 2010 from http://en.wikipedia.org/wiki/Countercurrent_exchange.
Asghari and Al-Dliwe (2006) "Optimization of Carbon Dioxide Sequestration and Improved Oil Recovery in Oil Reservoirs" University of Regina, Saskatchewan, Canada, S4S 0A2.
Kuuskraa et al. (Feb. 2006) "Evaluating the Potential for 'Game Changer' Improvements in Oil Recovery Efficiency from CO2 Enhanced Oil Recovery" Prepared for U.S. Department of Energy Available Web Site: http://fossil.energy.gov/programs/oilgas/publications/eor_co2/Game_Changer_Document_2_06_with_appendix.pdf Accessed on Jan. 31, 2012.
Notice of Allowance mailed Dec. 16, 2009 with respect to U.S. Appl. No. 11/751,011 (US 2008/0283249).
Notice of Allowance mailed Dec. 3, 2009 with respect to U.S. Appl. No. 11/751,028 (US 2008/0283247).

*Primary Examiner* — Sikarl Witherspoon
(74) *Attorney, Agent, or Firm* — Merchant Gould P.C.

(57) ABSTRACT

Systems, catalysts, and methods are provided for transforming carbon based material into synthetic mixed alcohol fuel.

14 Claims, 8 Drawing Sheets

U.S. PATENT DOCUMENTS

| | | | |
|---|---|---|---|
| 6,032,456 A | 3/2000 | Easom et al. |
| 6,159,434 A | 12/2000 | Gonjo et al. |
| 6,168,054 B1 | 1/2001 | Shelton, Jr. |
| 6,306,917 B1 | 10/2001 | Bohn et al. |
| 6,328,104 B1 | 12/2001 | Graue |
| 6,413,479 B1 | 7/2002 | Kudo et al. |
| 6,431,840 B1 | 8/2002 | Mashimo et al. |
| 6,458,478 B1 | 10/2002 | Wang et al. |
| 6,503,649 B1 | 1/2003 | Czajkowski et al. |
| 6,505,467 B1 | 1/2003 | Fjellhaug et al. |
| 6,506,359 B1 | 1/2003 | Maruko |
| 6,581,684 B2 | 6/2003 | Wellington et al. |
| 6,653,005 B1 | 11/2003 | Muradov |
| 6,821,501 B2 | 11/2004 | Matzakos et al. |
| 6,893,755 B2 | 5/2005 | Leboe |
| 6,899,859 B1 | 5/2005 | Olsvik |
| 6,986,797 B1 | 1/2006 | Clawson et al. |
| 7,040,390 B2 | 5/2006 | Tubel et al. |
| 7,056,482 B2 | 6/2006 | Hakka et al. |
| 7,064,097 B1 * | 6/2006 | Cai et al. ................... 502/342 |
| 7,066,973 B1 | 6/2006 | Bentley et al. |
| 7,067,456 B2 | 6/2006 | Fan et al. |
| 7,089,907 B2 | 8/2006 | Shinagawa et al. |
| 7,100,692 B2 | 9/2006 | Parsley et al. |
| 7,156,886 B2 | 1/2007 | Nakamura et al. |
| 7,168,488 B2 | 1/2007 | Olsvik et al. |
| RE39,675 E | 6/2007 | Kudo et al. |
| 7,272,934 B2 | 9/2007 | Chandran et al. |
| 7,481,275 B2 | 1/2009 | Olsvik et al. |
| 7,506,685 B2 | 3/2009 | Zubrin et al. |
| 7,562,708 B2 | 7/2009 | Cogliandro et al. |
| 7,624,801 B2 | 12/2009 | Zubrin et al. |
| 7,650,939 B2 | 1/2010 | Zubrin et al. |
| 7,654,330 B2 | 2/2010 | Zubrin et al. |
| 7,753,972 B2 | 7/2010 | Zubrin et al. |
| 7,810,565 B2 | 10/2010 | Zubrin et al. |
| 7,918,906 B2 | 4/2011 | Zubrin et al. |
| 7,931,712 B2 | 4/2011 | Zubrin et al. |
| 7,937,948 B2 | 5/2011 | Zubrin et al. |
| 8,047,007 B2 | 11/2011 | Zubrin et al. |
| 2001/0047040 A1 | 11/2001 | Agee et al. |
| 2002/0077374 A1 | 6/2002 | Jackson et al. |
| 2002/0083644 A1 | 7/2002 | Sata et al. |
| 2002/0083646 A1 | 7/2002 | Deshpande et al. |
| 2002/0090327 A1 | 7/2002 | Deshpande |
| 2002/0182462 A1 | 12/2002 | Ballantine et al. |
| 2003/0008186 A1 | 1/2003 | Dickman et al. |
| 2003/0037928 A1 | 2/2003 | Ramachandran et al. |
| 2003/0051405 A1 | 3/2003 | Childress et al. |
| 2003/0070808 A1 | 4/2003 | Allison |
| 2004/0161377 A1 | 8/2004 | Davey |
| 2004/0163311 A1 | 8/2004 | Ahmed et al. |
| 2004/0256116 A1 | 12/2004 | Olsvik et al. |
| 2005/0039400 A1 | 2/2005 | Lau et al. |
| 2005/0210881 A1 | 9/2005 | Balan et al. |
| 2006/0054318 A1 | 3/2006 | Sarada |
| 2006/0213657 A1 | 9/2006 | Berchenko et al. |
| 2006/0272813 A1 | 12/2006 | Olsvik et al. |
| 2007/0004588 A1 * | 1/2007 | Wang et al. ................... 502/174 |
| 2007/0099038 A1 | 5/2007 | Galloway |
| 2007/0130957 A1 | 6/2007 | Hoffmann et al. |
| 2007/0220810 A1 | 9/2007 | Leveson et al. |
| 2008/0053655 A1 | 3/2008 | Retallick et al. |
| 2008/0296018 A1 | 12/2008 | Zubrin et al. |
| 2009/0123364 A1 | 5/2009 | Forsyth et al. |
| 2009/0158701 A1 | 6/2009 | Hoffmann et al. |
| 2009/0236093 A1 | 9/2009 | Zubrin et al. |
| 2010/0314136 A1 | 12/2010 | Zubrin et al. |
| 2011/0088896 A1 | 4/2011 | Preston |
| 2011/0088897 A1 | 4/2011 | Raman |

FOREIGN PATENT DOCUMENTS

* cited by examiner

Fig. 1

Comparison of Energy of Pioneer Synthetic Fuel (PSF) with Alternatives

Process Flow Diagram for PSF Experimental Testing
*Fig. 2*

The test reactor
*Fig. 3*

The test apparatus

*Fig. 4*

Feed to 8-hr Ethanol to Butanol Production Run (wt%)

*Fig. 5*

Products from 8-hr Ethanol to Butanol Production Run (wt%)

Corn ethanol production in the USA, 1980 to 2006. (Source Energy Information Administration, http://www.eia.doe.gov)

Capitol costs for various chemical plants. Adapted to current dollars from Perry's Chemical Engineer's Handbook, 7th ed.

METHODS OF HIGHER ALCOHOL SYNTHESIS

RELATED APPLICATIONS

This application claims priority to U.S. Provisional Application Ser. No. 61/081,578 filed Jul. 17, 2008 and entitled "Novel Methods of Higher Alcohol Synthesis", the disclosure of which is hereby incorporated by reference in its entirety.

This invention was made with Government support under contract NAS9-98030 awarded by NASA. The Government has certain rights in this invention.

TECHNICAL FIELD

The present disclosure relates to systems, methods, and catalysts used to generate synthetic mixed alcohol fuels.

BACKGROUND

The statements in this section merely provide background information related to the present disclosure and may not constitute prior art.

While the US corn ethanol industry is a clear and growing success, it faces a number of issues. In the first place, the Renewable Fuels Standard (RFS) signed into law in 2005 will cap corn ethanol growth at 15 billion gallons/year, an insufficient amount given the world's need for ethanol. Even if that regulation should be repealed, however, its growth would be limited by the availability of corn for feedstock. In order to produce the 8 billion gallons it manufactured in 2007, the corn ethanol industry had to employ 20% of all corn-farm acreage in the USA for its purpose. Thus, there are clearly limits to corn ethanol production, regardless of governmental regulation. Furthermore, while the effect of the corn-ethanol program on retail food prices is debatable (given the small fraction that commodity prices partake of retail food costs), there can be little question that the corn-ethanol program is driving up corn commodity prices, and thus the cost of its own feedstock. In addition, corn commodity prices are driven by oil prices, which feed into fertilizer process, farm vehicle and pump operating costs, and transport costs. Thus, as the price of oil rises, so do the feedstock costs of the corn ethanol industry (with corn rising from $2.50/bushel to $7/bushel over the past three years, for example), and these costs are estimated to comprise 70% of the cost of their product. Thus, if the ethanol industry is limited to corn feedstock, both its size, and its potential profitability will remain limited, regardless of how high the price of oil rises.

The present invention is directed toward overcoming one or more of the problems discussed above.

SUMMARY

Provided herein are innovations that enable abundant renewable fuels. Some embodiments include a catalyst for transforming any carbon rich material—including all forms of biomass without exception—into a synthetic mixed alcohol fuel (hereinafter, PSF) suitable for use in automobiles. PSF is a mixture of alcohols, including methanol, ethanol, propanol, and butanol, and a variety of gasoline-type light hydrocarbons.

Other embodiments provide a process of reacting methanol with ethanol or propanol to produce butanol. In some aspects, the ethanol to butanol (EtB) process can be used to upgrade either PSF or methanol and ethanol produced by conventional means into butanol, which is a superior fuel.

Also provided are catalysts and reactions for producing PSF and butanol.

BRIEF DESCRIPTION OF THE DRAWINGS

The drawings described herein are for illustration purposes only and not intended to limit the scope of the present disclosure in any way.

DETAILED DESCRIPTION

The following description is merely exemplary in nature and is in no way intended to limit the present disclosure, application, or uses.

Provided herein are methods of producing liquid fuel from synthesis gas. The synthesis gas can be reacted at pressures between 500 and 3000 psi and at temperatures between about 200° C. and about 400° C. over a catalyst. In some embodiments, the catalyst includes copper, zinc, and potassium on a substrate. In other embodiments, the catalyst includes copper, zinc, and potassium with the addition of either or both manganese or cobalt on a substrate. Exemplary substrates include aluminum oxide, silica, and carbon nanotubes. Other combinations are contemplated herein.

The liquid fuel produced from such a process includes a mixture of alcohols and hydrocarbons, including but not limited to methanol, ethanol, propanol, butanol, and others. This liquid fuel is described herein as "PSF". In some embodiments PSF is a combination of methanol, higher alcohols and hydrocarbons, and in particular a combination of about 20% to about 60% methanol and about 80% to about 40% higher alcohols and hydrocarbons by volume. In other embodiments, PSF is a combination of about 40% to about 80% methanol and about 60% to about 20% higher alcohols and hydrocarbons by volume. Illustrative higher alcohols include ethanol, propanol, butanol and the like; illustrative hydrocarbons include propane, butane and the like. Percentages of different alcohols and hydrocarbons vary dependent upon reaction conditions as described herein, for example higher pressures and higher ratios of carbon monoxide to hydrogen in the reactor feed will lead to higher ratios of higher alcohols relative to methanol in the product.

In some aspects, it can be desirable to increase the energy content of a fuel generated according to the methods described herein. This can be achieved, for example, by removing the methanol component of a fuel by distillation.

Also provided herein are methods of producing butanol by reacting methanol with either or both ethanol or propanol. In some embodiments, the reaction occurs at a pressure under 3000 psi and temperatures between about 200° C. and about 400° C., and in some aspects, a catalyst can be present. Exemplary catalysts include copper on hydrotalcite. In some aspects, the hydrotalcite is a basic variety and has a magnesium oxide (MgO) to aluminum oxide ($Al_2O_3$) ratio greater than 1:1. In some aspects, the hydrotalcite comprises carbon nanotubes. Magnesium ethoxide or an MgO nanomaterial can be the source of magnesium in the catalyst. The source for Al and/or Cu can be nanomaterials.

Using the above described catalyst, a molecular template for ethanol can be created by evaporating ethanol from the catalyst suspension. The catalyst can be calcined in flowing air or a mixture of gases containing oxygen for about 2 to about 10 hours at a temperature between about 200° C. and 1000° C.

The methanol used according to this method can be produced by reacting synthesis gas on a copper and zinc catalyst. In some aspects, the synthesis gas is reacted at pressures between atmospheric pressure and about 3000 psi and at temperatures between about 200° C. and about 400° C.

Reaction components can be generated from readily available materials such as biomass. For example, ethanol can be produced from corn or sugar Likewise, synthesis gas can be produced from corn stover, bagasse, or other sugar cane crop residues. It is contemplated herein that synthesis gas can be produced from various biomass sources, including but not limited to forest and mill residues, agricultural crops and wastes, brush, hay, straw, switch grass, corn stalks, corn stover, kudzu, grass, wood and wood wastes including wood chips and sawdust, pine beetle kill, animal wastes, livestock operation residues, paper waste, paper mill process effluent, paper, cardboard, aquatic plants, algae, fast-growing trees and plants, organic landfill wastes, municipal, residential, industrial wastes, and any other source of cellulosic material. One of skill in the art would understand that as used herein, the term "biomass" includes combinations of various biomass sources, and further that biomass can be used in combination with other fuel/hydrocarbon sources.

Further provided are methods of producing a mixture of butanol and higher alcohols and hydrocarbons from synthesis gas. The synthesis gas can be reacted at pressures between 500 and 3000 psi, for example, between 600 psi and 3000 psi, between 600 psi and 2000 psi, or between 700 psi and 2000 psi, and temperatures between about 200° C. and about 400° C. In some embodiments, a catalyst can be used. In some aspects, the catalyst can include copper, zinc, and potassium on a substrate. In other aspects, the catalyst can include copper, zinc, potassium, and one or both of manganese or cobalt on a substrate. Illustrative substrates include silica, carbon nanotubes, and aluminum oxide. The method generates a mixture of alcohols and hydrocarbons, including, but not limited to, methanol, ethanol, propanol, and butanol. The methanol in the mixture is then reacted with the ethanol and/or propanol components of PSF to produce butanol. In some aspects, this reaction is performed at pressures under 3000 psi, such as, for example, pressures between atmospheric pressure and 100 psi, 100 psi and 500 psi, 100 psi and 3000 psi, 200 and 3000 psi, and 500 psi and 3000 psi, and temperatures between about 200° C. and about 400° C. In some embodiments, a catalyst can be used. This catalyst can be, for example, copper on hydrotalcite. In some aspects, the hydrotalcite is of a basic variety with an MgO to $Al_2O_3$ ratio greater than 1:1.

Synthesis gas can be produced from a variety of products. In some aspects, the synthesis gas is produced by steam reformation of biomass, for example, by steam reformation of corn stover. In other aspects, the synthesis gas is produced by steam reformation of lignin or hemicellulose available as waste from cellulosic ethanol production. In still other aspects, the synthesis gas is produced by steam reformation of forestry residues and/or other sources of wood products. And in still more aspects, synthesis gas is produced by steam reformation of algae, for example, algae grown in specially designed algae farms and/or algae harvested from commercial fish ponds, natural sources, and water treatment plants.

It is contemplated herein that synthesis gas can be produced by steam reformation of any biomass source, including but not limited to forest and mill residues, agricultural crops and wastes, brush, hay, straw, switch grass, corn stalks, corn stover, kudzu, grass, wood and wood wastes including wood chips and sawdust, pine beetle kill, animal wastes, livestock operation residues, paper waste, paper mill process effluent, paper, cardboard, aquatic plants, algae, fast-growing trees and plants, organic landfill wastes, municipal, residential, industrial wastes, any other source of cellulosic material, and any mixtures thereof.

In some embodiments, the synthesis gas is produced by steam reformation of coal. In other embodiments, the synthesis gas is produced by steam reformation of natural gas or landfill gas. In still other embodiments, the synthesis gas is produced by steam reformation of trash.

In further embodiments, the synthesis gas is produced by using a reverse water gas shift to convert $CO_2$ to CO. In some aspects, waste $CO_2$ and hydrogen produced by the methods described herein are converted back into CO by using reverse water gas shift. The CO is then recycled for use as synthesis gas.

PSF Energy Content

Figure 1:
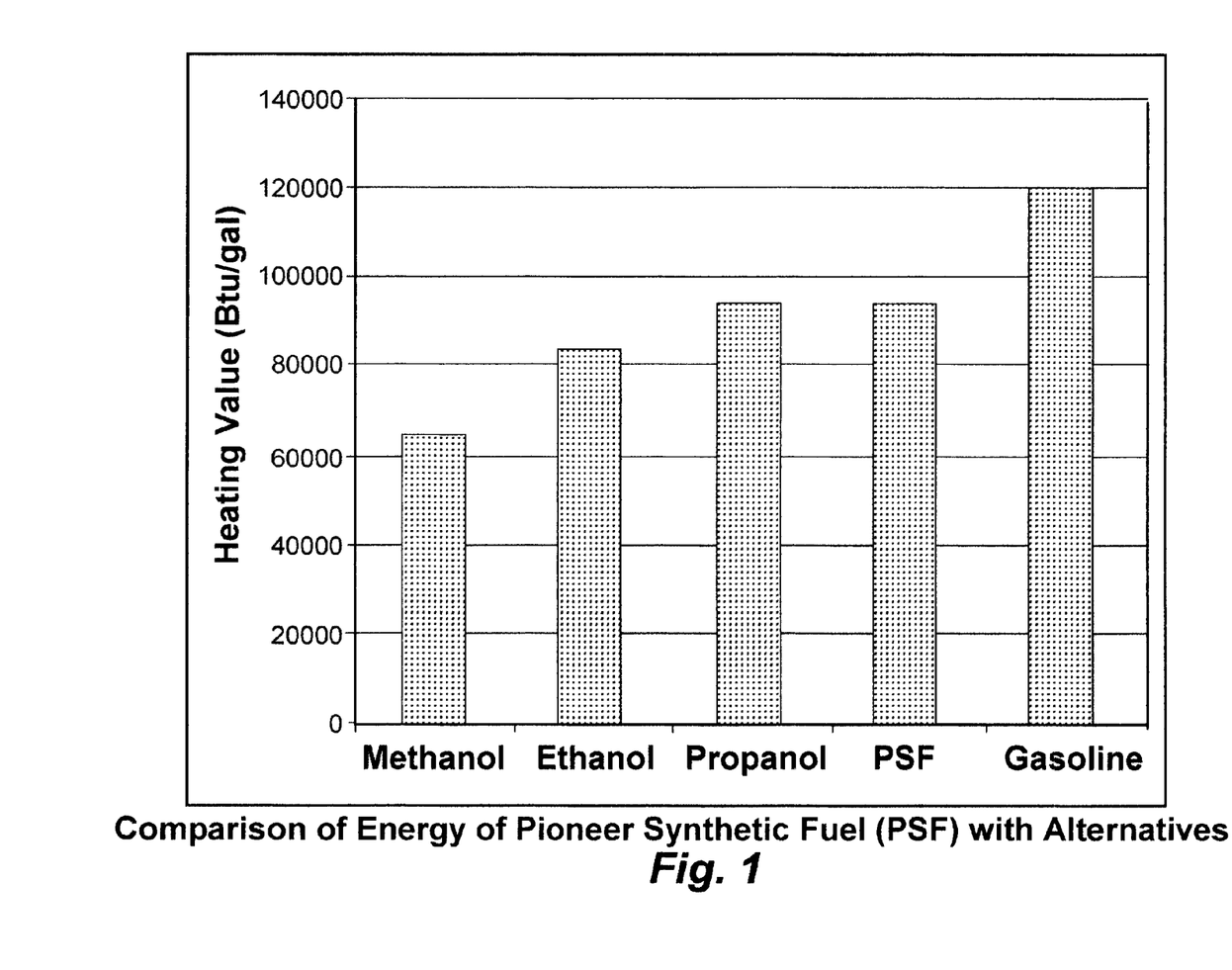
FIG. 1 is a graphical comparison of heating values (Btu/gal) for methanol, ethanol, propanol, embodiments of Pioneer Synthetic Fuel (PSF), and gasoline.

FIG. 1 shows how PSF compares to other fuels in terms of energy content. It can be seen that PSF has about 111% the energy content of ethanol. However, unlike ethanol, the manufacture of PSF is not limited to the use of corn, sugar, or other food crops for feedstock but can be done from a variety of low cost feeds including weeds, crop residues, spoiled crops, fallen leaves, forestry wastes, swamp plants, seaweed, algae, other biomass sources, coal, natural gas, recycled urban trash, and mixtures thereof.

Manufacture of PSF

In one embodiment herein, PSF is manufactured in two steps. The first step is to react carbonaceous material with steam to turn it into synthesis gas, or "syngas" which is a mixture of carbon monoxide (CO) and hydrogen ($H_2$). Such "steam reformation" reactions are well understood, and have been widely practiced by engineers since the gaslight era. Some examples include reactions 1-3:

$C+H_2O=>CO+H_2$                  (1) Steam reformation of Coal $C_4H_6O_3+H_2O=>4CO+4H_2$      (2) Steam reformation of Biomass $CH_4+H_2O=>CO+3H_2$               (3) Steam Reformation of Methane In general, steam reformation reactions require some heat energy to be driven. This energy can be readily supplied, for example, by burning a minority of the feedstock.

Catalysts can be used to transform syngas into methanol ($CH_3OH$), via reaction 4.

$CO+2H_2=CH_3OH$                       (4) Methanol manufacture.

Reaction (4) can be performed at readily achievable pressures and temperatures (1000 psi, 260° C.). However, as seen is FIG. 1, methanol has the lowest energy content of any liquid fuel (only 75% that of ethanol). Disclosed herein is also a new low-cost combined metal catalyst that can turn syngas into higher alcohols, for example propanol ($C_3H_7OH$). Under similar conditions, older catalysts just make methanol. Propanol manufacture is shown in reaction 5:

$$5CO + 4H_2 => C_3H_7OH + 2CO_2 \quad (5) \text{ Propanol manufacture}$$

Propanol is a much better fuel than methanol, having 111% the energy content of ethanol. The catalyst disclosed herein does not make pure propanol, but a mixture of alcohols, including methanol, ethanol, propanol, butanol, higher alcohols, and some gasoline-type hydrocarbons. The average energy content of an exemplary mixture, however, is about equal to that of propanol. If desired, the methanol content (~25%) can be removed to create a fuel with 123% the energy of ethanol. The methanol can then be sold for industrial use.

Ethanol to Butanol (EtB) Production Process

Described herein is a second catalytic process that allows the reaction between the methanol in PSF with the ethanol and propanol to make butanol ($C_4H_9OH$). This raises the energy content of PSF well above butanol levels (120% ethanol). This process can also be used to upgrade ethanol produced by other means (i.e. the existing corn ethanol industry), increasing both the quantity and quality of its product. Not only does butanol have a higher energy content than lower alcohols, it offers the additional advantages of being usable in high concentration in both existing gasoline and diesel engines, and transportable in existing pipelines.

Alumina felt and zirconia foam (214) provide additional catalytic features to the process reaction.

Commercial Potential

Figure 7:
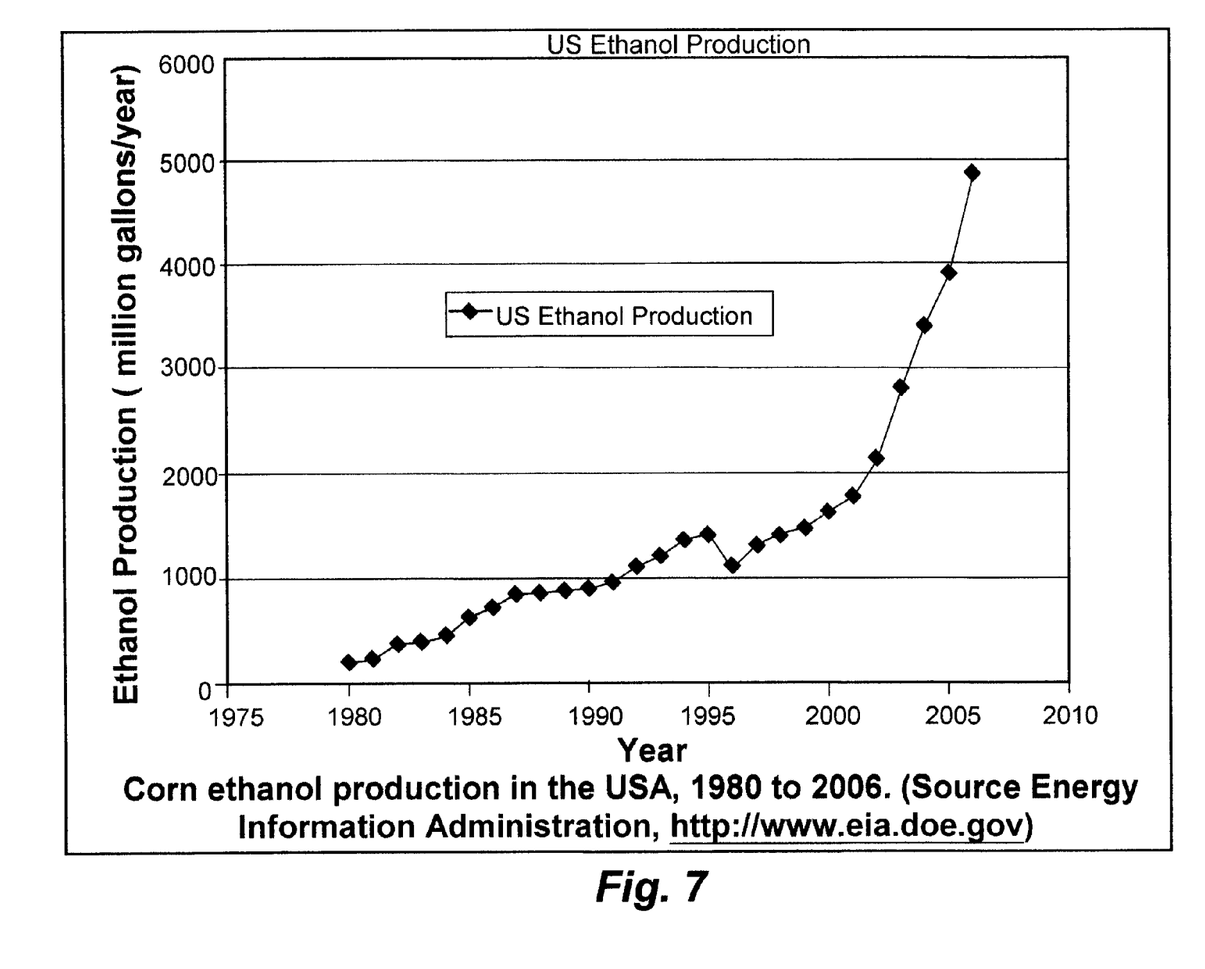
FIG. 7 demonstrates corn ethanol production in the U.S. from 1980 to 2006.
Figure 8:
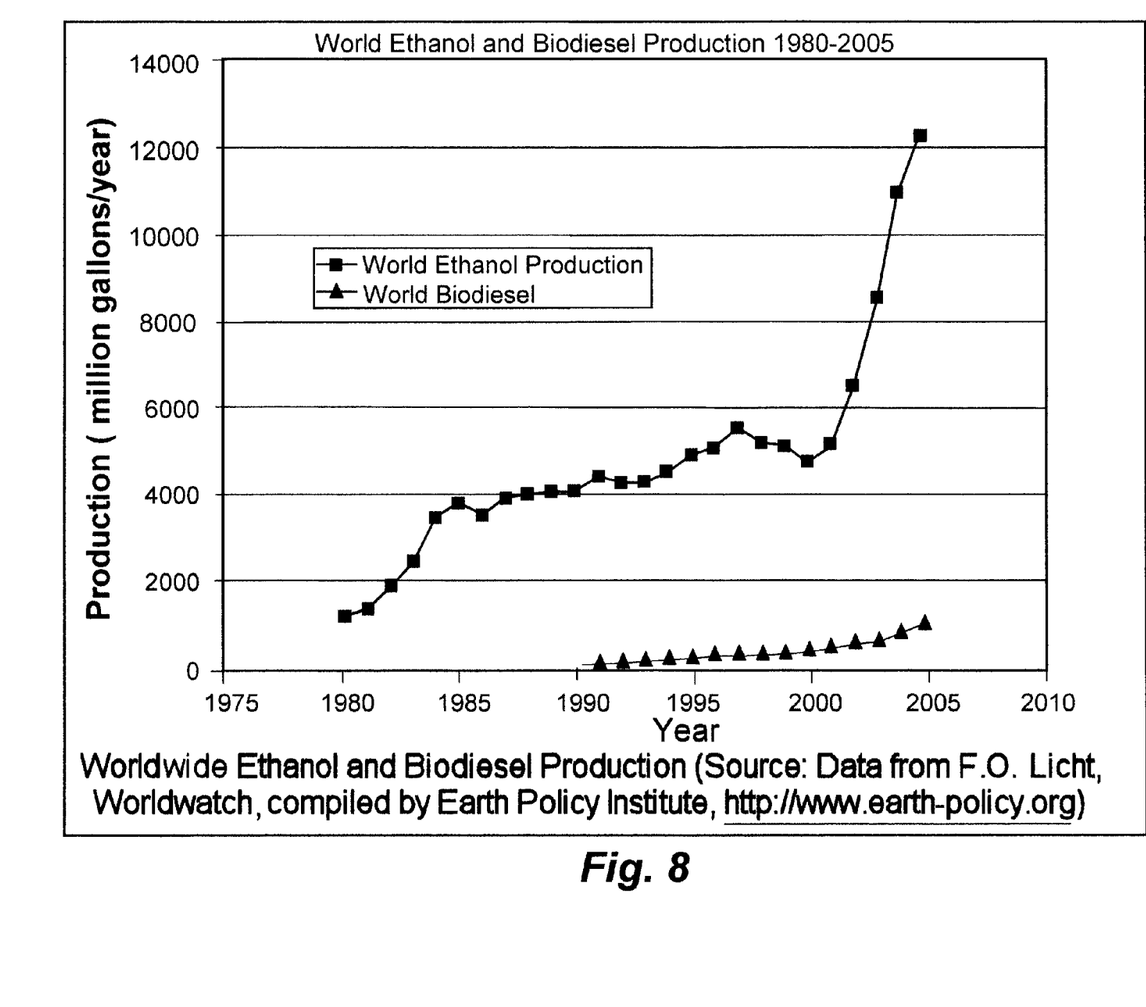
FIG. 8 demonstrates worldwide ethanol and biodiesel production from 1980 to 2005.

As world demand for vehicle fuels continue to grow, and gasoline, diesel fuel, and oil prices continue to rise, both US and global production of biofuels have risen exponentially. This is shown in FIGS. 7 and 8, which report data from public sources through 2006.

Since 2006, the rate of growth has been even more rapid, with total US corn ethanol production reaching 8 billion gallons in 2007, a 60% rise from the previous year. Rapid growth can be expected to continue, since on Dec. 19, 2007, the Energy Independence and Security Act of 2007 (H.R. 6) was signed into law. This comprehensive energy legislation amends the Renewable Fuels Standard (RFS) signed into law in 2005, growing the amount of biofuel required for admixture into the US vehicle fuel supply to nearly double to 15.2 billion gallons by 2012, and then goes to 24 billion gallons by 2017, and 36 billion gallons by 2022. Of the 36 billion gallons required in 2022, the law specifies that at most 15 billion gallons can come from conventional corn ethanol, while the additional 21 billions must come from cellulosic or other non-food based sources. The law also provides a subsidy of $0.45/gallon for all biofuel produced in the USA.

The government mandated RFS Targets are set forth in Table 4.

TABLE 4

RFS Biofuel Production Requirements

| Year | Renewable Biofuel | Advanced Biofuel | Cellulosic Biofuel | Biomass-based Diesel | Undifferentiated Advanced Biofuel | Total RFS |
|---|---|---|---|---|---|---|
| 2008 | 9.0 | | | | | 9.0 |
| 2009 | 10.5 | .6 | | .5 | 0.1 | 11.1 |
| 2010 | 12 | .95 | .1 | .65 | 0.2 | 12.95 |
| 2011 | 12.6 | 1.35 | .25 | .8 | 0.3 | 13.95 |
| 2012 | 13.2 | 2 | .5 | 1 | 0.5 | 15.2 |
| 2013 | 13.8 | 2.75 | 1 | | 1.75 | 16.55 |
| 2014 | 14.4 | 3.75 | 1.75 | | 2 | 18.15 |
| 2015 | 15 | 5.5 | 3 | | 2.5 | 20.5 |
| 2016 | 15 | 7.25 | 4.25 | | 3.0 | 22.25 |
| 2017 | 15 | 9 | 5.5 | | 3.5 | 24 |
| 2018 | 15 | 11 | 7 | | 4.0 | 26 |
| 2019 | 15 | 13 | 8.5 | | 4.5 | 28 |
| 2020 | 15 | 15 | 10.5 | | 4.5 | 30 |
| 2021 | 15 | 18 | 13.5 | | 4.5 | 33 |
| 2022 | 15 | 21 | 16 | | 5 | 36 |

System Embodiments

In some embodiments, systems are provided for production of PSF. Systems embodiments herein provide a reactor having a catalyst integrated therein. Catalyst can be fixed bed in the reactor. One or more thermocouples can be included in the reactor to monitor catalyst bed temperatures. Additional thermocouples can be outside the reactor to monitor exit gas temperature and reactor shell temperature.

Figure 2:
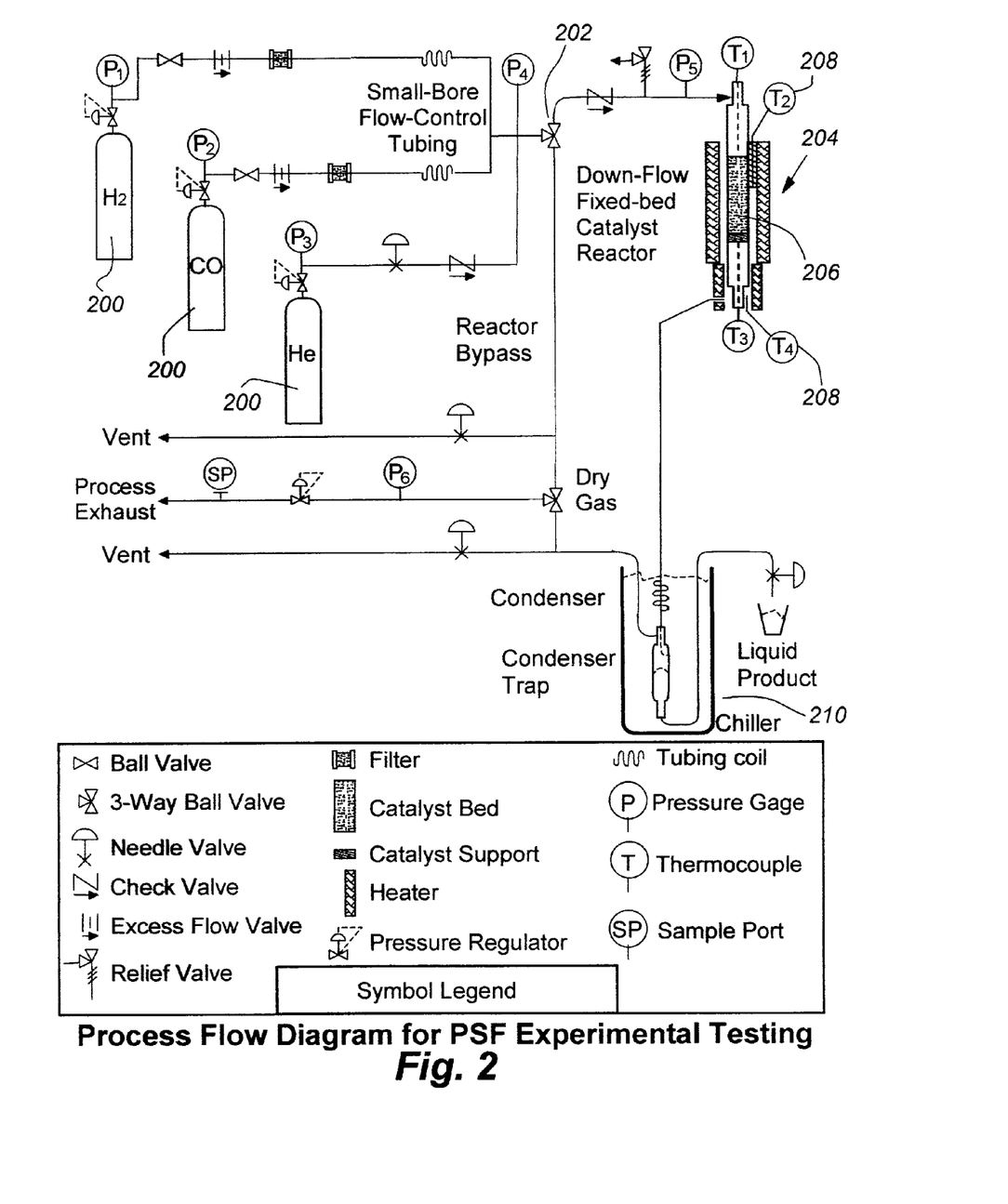
FIG. 2 is a flow chart illustrating the bench scale system used to test catalysts.
Figure 3:
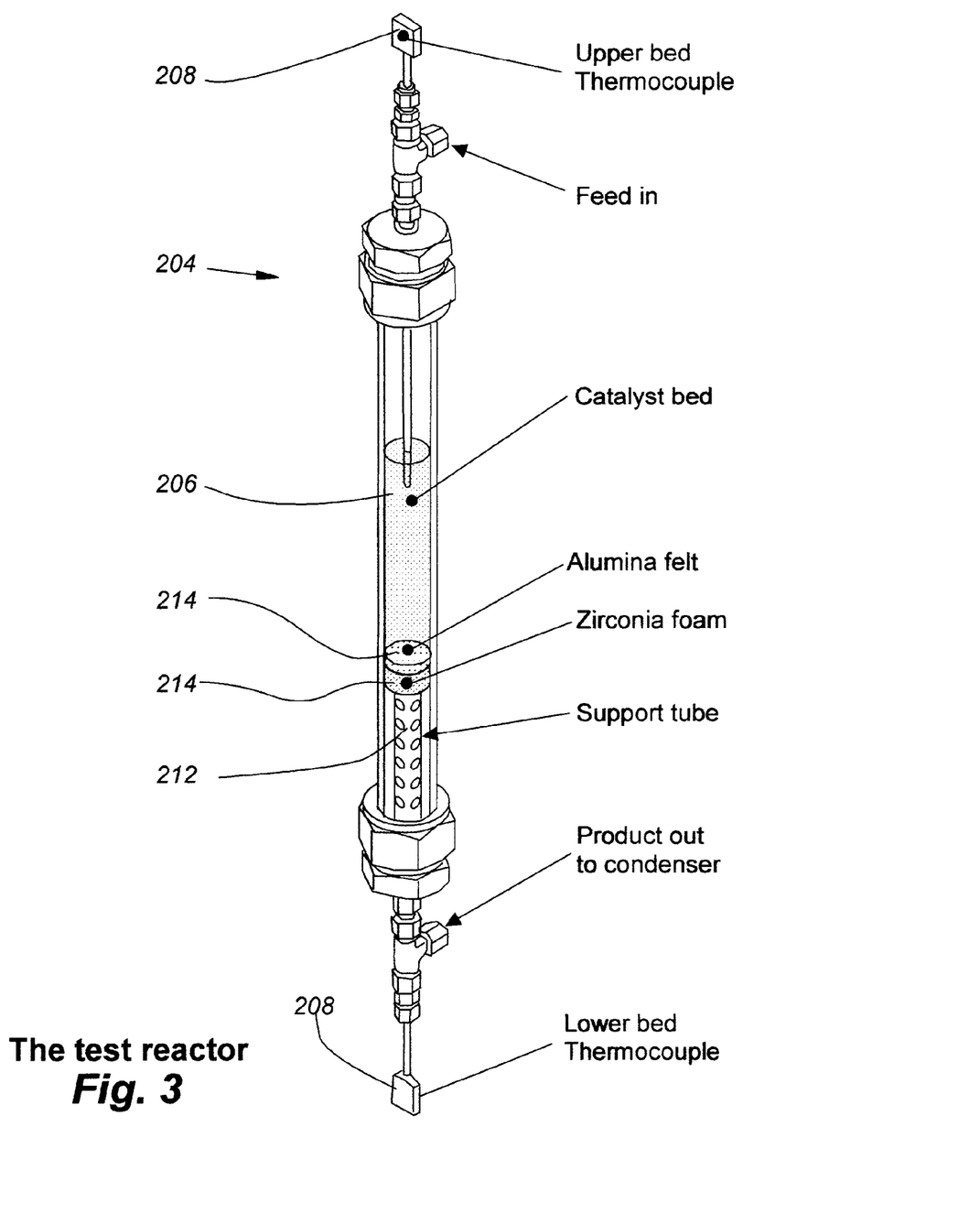
FIG. 3 is a drawing of the test reactor.

Referring to FIG. 2, $H_2$, CO and the gases (or other synthesis gas) (200) are fed through one or more flow controls (202) and into a reactor (204) in accordance with the present invention. Catalyst (206) in accordance of the invention is trapped within the reactor. Thermocouples (208) are shown. Liquid product and process exhaust are separated via condenser (210) or other like apparatus. FIG. 3 provides additional detail for an illustrative reactor embodiment herein. A reactor (204) has a series of thermocouples (208) and catalyst bed (206) in accordance with embodiments herein. A support tube (212) avoids compaction of the catalyst in the reactor.

There is a huge and growing government mandated market for biofuels in the USA. In fact, as a result of high oil prices, the industry has actually been growing faster than the targets required for it by the RFS. It is evident that a vast market for biofuels is clearly present, even without the mandate. However, the following facts should be noted:

Almost all the growth of ethanol production so far has been in conventional corn ethanol, while the new RFS requires large majority of the future growth to be in biofuels produced from non-fuel sources. This need can be met by PSF.

The RFS caps the production of corn-based biofuel at 15 billion gallons, a target it can be expected to reach in less than 4 years. So if corn-ethanol producers want to continue to expand the income from their corn-based product, they will need to increase the monetary value of their product on a dollar/gallon basis. This could be done by converting their ethanol to butanol, through the ethanol to butanol process described herein.

The growing demand for biofuels defined by world oil prices and global fuel needs, and required in the USA regardless by the RFS, ensures a vast potential market for PSF and butanol products. Furthermore, the requirements laid out in the RFS strongly favor embodiments herein, as continued expansion of the biofuel industry using conventional approaches will not be possible.

At a price of $3/gallon, the RFS will require the use of over $100 billion in biofuels every year in the USA alone, with the majority produced by non-conventional means. This may be a very conservative estimate of the market size, since most analysts project that the price of gasoline, and thus the value of biofuels, will continue to rise strongly in the future.

Economic Analysis

Figure 9:
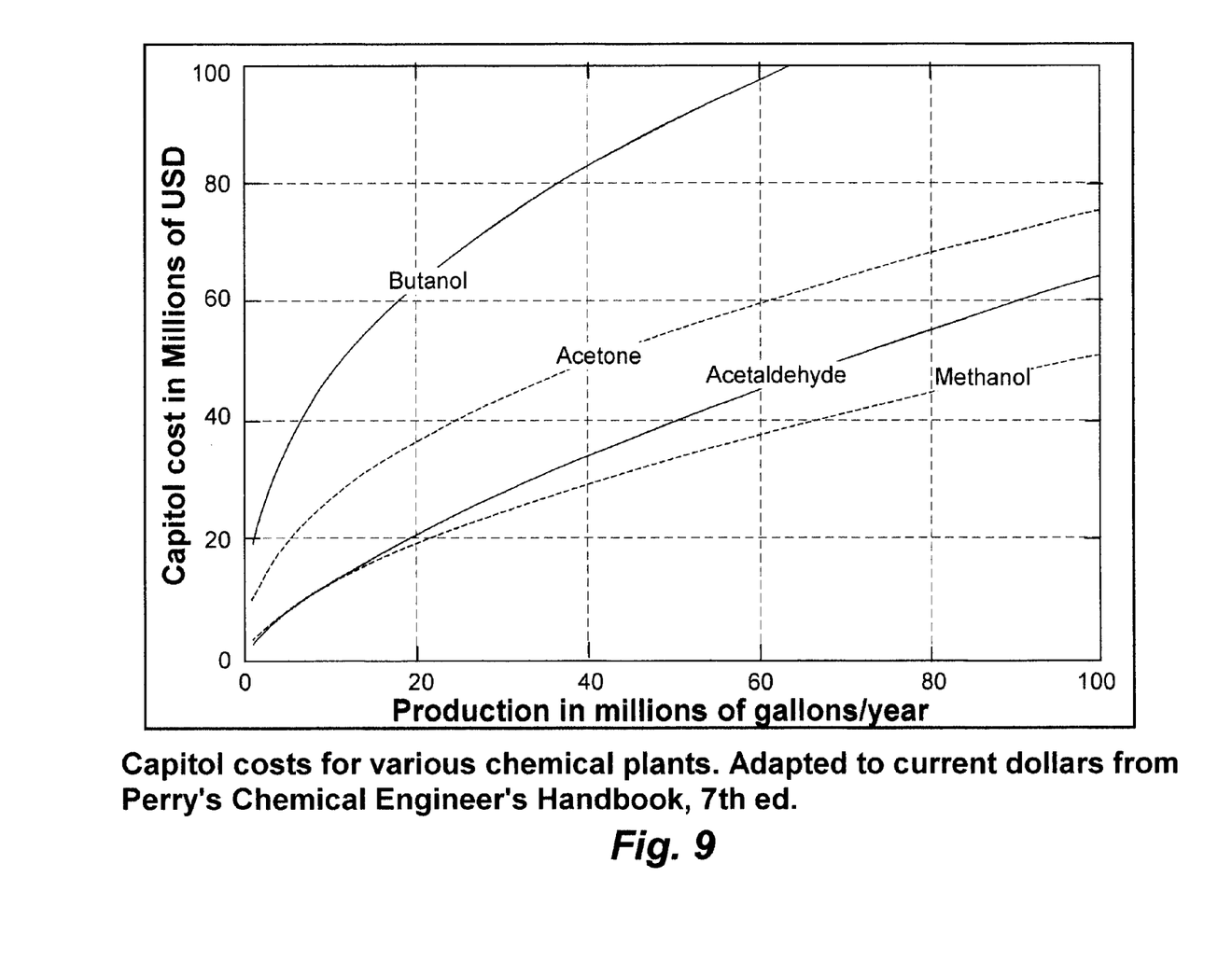
FIG. 9 compares capital costs for butanol, acetone, acetaldehyde, and methanol chemical plants.

An initial estimate for the capital cost of an ethanol-to-butanol plant can be made by comparing the capital costs of similar chemical plants as shown in FIG. 9. The capital cost for a methanol plant are relatively low at about $0.70/gallon at 60 million gallons/year whereas a butanol plant (using petrochemical technology) is much more expensive at about $1.55/gallon at the same production rate.

Assuming that an ethanol-to-butanol plant will have a capital cost equal to the average of the range of current chemical plants (about $1.20 per gallon per year), and assuming an 8% per year cost of money, then the interest cost on capital investment will be about $0.10 per gallon. The current value of methanol is $1.50 per gallon; ethanol is about $2.20/gallon, while butanol is worth $3.50 per gallon. This process turns 0.86 gallons of methanol (worth $1.30 at commercial prices) plus 0.62 gallons of ethanol (worth $1.37) into one gallon of butanol (worth $3.50) for a total gain of $0.83 per gallon of butanol produced. If the cost of the methanol is discounted, since it can be made at the ethanol-to-butanol plant itself from crop residues with close to zero feedstock costs, then the gain could be as much as $2.13 per gallon of butanol produced. This is a surprising utility for the methods any systems described herein.

So even if the capital cost is twice as much as the average of the current state of the art, the interest cost on capital investment ($0.20/gallon of butanol produced) will be only a quarter of the monetary gain per gallon, under the most conservative scenario of pricing the methanol used at commercial market prices, and less than a tenth of the gain if the methanol is discounted as a product of the plant itself.

In the case of making butanol from PSF, embodiments herein, or simply using PSF itself, the economics are potentially even more favorable, as all the fuel is made from crop residue feedstocks with near zero cost. Thus the dominant element of the cost will be interest on capital, which, under conservative scenarios is unlikely to exceed $0.20/gallon of fuel produced. In contrast, the expenses of the existing corn ethanol industry are dominated by the price of the corn feedstock, which comprises 70% (>$1.50/gallon) of the entire cost of production. The extra capital cost of the PSF process is thus made up for many times over by the elimination of the much greater cost of corn feedstock.

Comparison of Cost and Profit

Table 5 shows a cost/profit comparison of conventional corn ethanol production with the inventive processes herein. The corn ethanol process is assumed to be using corn at a price of $6/bushel, (somewhat lower than the $7/bushel prevailing in July 2008, equal to $0.107/lb), while raw biomass used by the PSF and butanol processes is assumed to be corn stover, priced at the current 50 mile range delivered cost of $40/dry metric tonne (equal to $0.018/lb). Capital cost is assumed to be based on per-process plant cost of $2 invested per gallon/yr produced at 7% interest. O&M cost is taken at $0.20/gal per process. For processes involving ethanol, the value of the by product distillers grain is included on the profit side of the ledger.

In Table 5, Option 1 is the current conventional corn ethanol industry. Option 2 takes the ethanol product from this industry, and reacts it with commercially purchased methanol to produce butanol using the processes as described herein. Option 3 reacts commercial corn ethanol with methanol produced from corn stover at the plant itself to make butanol. Option 4 produces PSF from corn stover as described herein. Option 5 takes PSF produced from corn stover and reacts its contents to produce butanol.

In Options 2 and 3 the extra process to include ethanol is not counted, since the cost of the ethanol itself is included as part of the feed cost.

TABLE 5

Cost and Profit Comparison of Alternative Processes

|  | Corn Ethanol | Ethanol to Butanol | Ethanol to Butanol | PSF | PSF to Butanol |
|---|---|---|---|---|---|
| Option Label | 1 | 2 | 3 | 4 | 5 |
| Feedstock | Corn Grain | Ethanol & Methanol | Ethanol & Stover | Stover | Stover |
| Cost of Feedstock | $2.18/gal | $2.67/gal | $1.49/gal | $0.35/gal | $0.35/gal |
| Cost of Capital | $0.14/gal | $0.14/gal | $0.28/gal | $0.14/gal | $0.28/gal |
| Cost of O&M | $0.20/gal | $0.20/gal | $0.40/gal | $0.20/gal | $0.40/gal |
| Total Cost | $2.52/gal | $3.01/gal | $2.17/gal | $0.59/gal | $1.03/gal |
| Value of Product | $2.20/gal | $3.50/gal | $3.50/gal | $2.40/gal | $3.50/gal |
| Val. of Byproduct | $0.58/gal | $0.36/gal | $0.36/gal | $0.00/gal | $0.00/gal |
| Govt. Subsidy | $0.45/gal | $0.45/gal | $0.45/gal | $0.45/gal | $0.45/gal |
| Gross Income | $3.23/gal | $4.31/gal | $4.31/gal | $2.85/gal | $3.95/gal |
| Net Profit | $0.71/gal | $1.30/gal | $2.14/gal | $2.26/gal | $2.92/gal |
| Profit w/o Subsidy | $0.26/gal | $0.85/gal | $1.69/gal | $1.81/gal | $2.47/gal |

It can be seen that the conventional corn ethanol process has a very narrow profit margin, which is only sustainable due to added revenue from the government subsidy and distiller's grain byproduct. In contrast, the processes (options 2 through 5) described herein, offer surprisingly much larger profit margins which are sustainable without government subsidy.

The Advantages of PSF and Butanol

In some embodiments, PSF process remedies one or more of the issues faced by the corn ethanol industry. Since PSF can be made from crop residues or other cellulosic (non-food) material, it can supply fuel outside of the 15 billion gallon limit set for corn ethanol by the RFS. Furthermore, since it can use any kind of biomass without exception for feedstock, (as well as coal, natural gas, dump gas, and recycled urban trash), its potential feedstocks are virtually unlimited, very cheap, and not susceptible to cost increases as the price of oil rises. Thus, as the price of oil continues to rise, PSF feedstock's costs will be fixed, and the profitability of PSF will rise relative to both oil and conventional corn ethanol.

PSF embodiments herein have a further advantage relative to ethanol in that it contains about 11% more energy per gallon, and thus is a higher quality fuel. Butanol is better still, having over 20% more energy per gallon than ethanol, but its qualitative advantages are even greater than such a comparison implies.

Ethanol cannot be used in diesel engines. Butanol can, which means it can be used to propel trucks, ships, trains, and diesel automobiles, which are becoming increasingly popular because of their high mileage capability. Ethanol cannot be shipped by the existing pipeline system, butanol can. This makes it much cheaper to transport, and therefore to market far away from the point of production. Ethanol cannot be used in concentrations of over ±15% in standard non-flex fuel cars. Butanol can readily be used by standard vehicles in mixes of over 60%. Ethanol is too low in energy to make it acceptable for use as aircraft fuel; butanol is energetic enough to be acceptable. Thus butanol is competitive with gasoline and diesel fuel across a range of applications and markets which are closed to ethanol. It is a better fuel than ethanol, and can fetch a higher price, from much larger markets worldwide.

The EtB process described herein can be used to make butanol either from ethanol or from PSF embodiments described herein. If used in combination with ethanol, it can greatly increase the value and marketability of the product of what will soon be a hundred billion dollar class global industry. If used in combination with the PSF manufacturing embodiments herein, it holds the potential to produce unlimited amounts of high quality renewable fuel from low cost resources whose utilization does not impact world food supplies in any way.

As gasoline and oil prices continue to climb, the world market is aggressively seeking new fuels. Under these conditions, ethanol, despite its modest energy content, has proven acceptable, and production of ethanol fuel is currently soaring. Ethanol, however, currently requires valuable food crops such as corn or sugar as feedstocks, which puts a floor under its production cost and an overall limit on the total production resource base available. In contrast, the embodiment described herein can be made from biomass, urban trash, or other zero-value or low-value feedstocks, and represents a fuel of superior quality to ethanol. In addition, the use of many of the potential feedstocks herein allows the production of fuel with no global warming impact. Using the EtB process described herein, ethanol produced either as a component of PSF embodiments or via conventional fermentation or enzymatic processes by the existing corn or emerging cellulosic ethanol industries can be converted to butanol, which is a superior fuel, usable in existing automobiles and transportable in existing pipelines. It is therefore believed that both PSF embodiments and EtB production processes offer extraordinary commercial potential.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Example 1

Experimental Testing of PSF Manufacture

Catalyst Preparation

Two catalysts have been manufactured. Both are metal catalysts using different combinations of low to mid cost metals deposited onto metal-oxide pellets. This catalyst formulation is easily adapted to industrial use since no expensive precious metals are required. The first catalyst involves a combination of 3 metals, copper, zinc, and potassium on an aluminum oxide substrate. The other catalyst involves 5 metals: copper, zinc, potassium, cobalt, and manganese. Other catalysts are contemplated, for example, four-metal catalysts combining the three metal catalyst with either cobalt or manganese, and substrates such as silica and carbon nanotubes.

Experimental Procedure

To test the catalyst, a bench scale system was designed to accommodate space velocities of 2000-4000 $hr^{-1}$ and operate at 1000 psi. Several sources indicated that higher quality products can be made operating at higher pressures; however, this would only improve the current product being made. The process flow diagram for this system is shown in FIG. 2.

Figure 4:
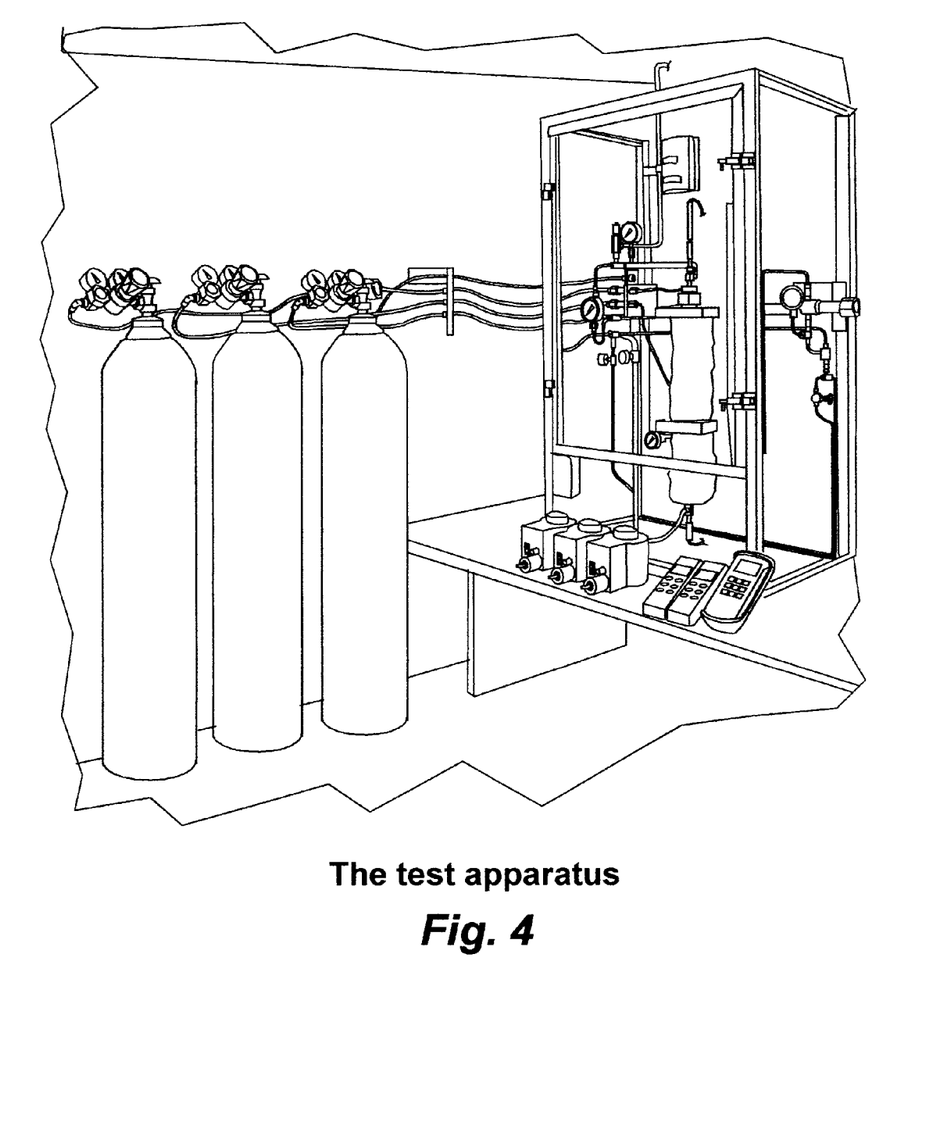
FIG. 4 illustrates an exemplary PSF generating system.

The system was designed and built around a reactor with a 100 cc catalyst volume. The reactor is a cylindrical, down flow, fixed bed design made of thick walled stainless steel tubing. (See FIG. 3) Two thermocouples are located inside the reactor to monitor the catalyst bed temperatures. One is positioned immediately after the catalyst bed below the zirconia foam used to retain the bed. The second extends about one inch into the catalyst at the top of the bed. There are two additional thermocouples monitoring temperatures outside the reactor. The shell thermocouple is on the outside of the reactor in the middle of the catalyst bed beneath the heat tape. The other is on the tee fitting prior to the gases exiting the reactor; this one is to ensure that the water and other condensable liquids are still in vapor form leaving the reactor. The entire test apparatus is shown in FIG. 4.

Based on the bulk density of the catalyst 90 g were sufficient to fill the 100 cc of desired catalyst volume. The catalyst was reduced in situ at a temperature of 598 K using a mixture of hydrogen and helium gas that was slowly increased in hydrogen concentration. The reduction was monitored by collecting water from the condenser and was assumed to be complete when no more water was collected. Seventeen tests were run in the PSF test stand. The following operating conditions were explored:

$H_2$:CO ratios from 0.5-1

Shell temperatures from 548-613 K

Pressure of 1000 psi

Gas hourly space velocities (GHSV) of 1850-3180 SL/kg catalyst/hr Additionally, the effect of including methane or carbon dioxide in the feed was investigated.

Prior to the start of each test the feed flow rate and composition were measured and recorded. The feed gases were then directed through the reactor and the system was allowed to run for about 30 minutes to achieve steady state operation. At this point the condensate was emptied and the actual test was begun. The temperatures were monitored constantly and recorded using thermometer data loggers. The exhaust flow rate was measured every 10-20 minutes using a bubble meter.

The exhaust gas composition was manually sampled and measured every 15-20 minutes using a GC with a thermal conductivity detector. The liquid condensate was also collected at several points during each test and its production rate noted. The composition of the liquid product from each run was also determined using the GC. The detector is not well suited for this task but was sufficient as a point of comparison. Peaks can be seen and identified corresponding to alcohols through C4. Several other small peaks representing various other hydrocarbons were present in some samples but these were not identified.

Results and Discussion

After several tests operating conditions were determined that resulted in a high quality product. In-house GC analysis showed its alcohol component to be about 50% volume methanol. The sample was then sent out for detailed hydrocarbon analysis to better characterize its composition. After replacing the catalyst a second test resulted in another high quality sample. The operating conditions and product information for both tests are shown in Table 2 below.

In Table 2, the upper and lower bed temperatures list ranges since both of these changed slightly during the course of each run. The shell temperature listed is the desired shell temperature, in reality this was plus or minus 5 K. For each test the average feed flow rate was calculated based on the average exhaust flow rate and the amount of liquid product made. The GHSV was then calculated by dividing the flow rate by the mass of catalyst in the reactor. The feed ratio ($H_2/CO$) was calculated based on the GC analysis of the feed stream prior to the start of the test. The mass of fuel made was divided by the mass of gases feed into the reactor during the test to determine the yield percent. The percent methanol in each sample is also listed.

TABLE 2

Sample PSF Production Results

| | Date | |
|---|---|---|
| | Day 0 | Day 56 |
| Length [minutes] | 95 | 90 |
| Temperatures [K] | | |
| Shell | 613 | 613 |
| Upper Bed | 438-430 | 453-448 |
| Lower Bed | 581-587 | 565-585 |
| GHSV [SL/kg cat/hr] | 2235 | 1986 |
| $H_2/CO$ | 0.67 | 0.73 |
| % Yield | 3.50% | 3.10% |
| % Methanol | | |
| of Alcohols | 50.00% | 57.80% |
| of Total | 30.16% | 36.24% |
| Heating Value [MJ/L] | 25614 | 25226 |

The first successful test had a shell temperature of 613 K with a feed ratio and GHSV of 0.67 and 2235 respectively. The upper bed temperature during this test was very similar to previous tests but the lower bed temperature reached a maximum of 590 K. The liquid yield during this test was 3.50%. In-house testing of the liquid product showed its alcohol fraction to be only 52% methanol. This sample was sent to an outside lab for analysis and it was determined to be in actuality only 30.16% methanol. Other major constituents (greater than 1% by volume) and their volume percent of the sample were the following:

Ethanol 2.5%
n-Propanol 11.7%
i-Propanol 1.3%
2-Butanol 11.3%
n-Butanol 1.9%
i-Propylcyclopentane 1.2%
1-Propylcyclopentane 1.2%

There were small amounts of t-Butanol, n-Pentanol, and n-Hexanol present as well. The remaining 38.8% of the sample consisted of various other hydrocarbons each less than 1 volume percent. This mixture has a heating value, measured following ASTM D6730, of 91,975 Btu/gal (25614 MJ/L). Gasoline has a heating value around 120,000 Btu/gal. Methanol and ethanol have heating values of 64,500 But/gal and 84,250 Btu/gal respectively. The heating value of the mixture is better than ethanol and comparable to Propanol (which has a heating value of 94,240 Btu/gal).

The first test after replacing the catalyst utilized similar operating conditions to the previous successful test. The reactor shell temperature was 613 K, the feed ratio was 0.73 and the space velocity was 1986 SL/kgcat/hr. The lower bed reached a maximum temperature of 585 K. Based on in-house analysis the alcohol fraction of this sample was 52.3% methanol. This sample was also sent for outside analysis so a comparison between this fuel and the previous desirable product could be made. This analysis showed that the two fuels were comparable. This one had slightly more methanol and some of the hydrocarbon components and concentrations varied somewhat but its heating value was still very respectable at 90583 But/gal. The major components (1 volume percent or more) are identified with their concentration as follows:

Methanol 36.24%
Ethanol 2.39%
Isopropanol 1.13%
1-Propanol 10.12%
2-Butanol 10.56%
Cyclohexane 1.29%
2,4-Dimethylhexane 2.02%

This sample also contained n-Butanol as did the previous sample but at only 0.35%. There were also small amounts of isobutanol, tert-butanol, n-Pentanol, n-Hexanol, and n-Heptanol detected totaling 1.23%. The remainder of the sample was again composed on various hydrocarbons less than 1% of the total volume each.

PSF Summary

The rig is capable of producing a liquid product that is 30 vol % methanol with the remainder being higher alcohols and hydrocarbons. This product has a heating value that is about 74% that of gasoline (or equivalently, 110% that of ethanol, or 148% that of methanol.) Thus, the operating conditions and catalyst that are capable of producing a superior fuel from synthesis gas. Since synthesis gas itself can be readily made from a wide variety of renewable, waste, or other low-cost feedstocks, such a process offers significant economic value.

Example 2

Biofuels Ethanol to Butanol (EtB) Production Process

Experimental Procedure

Biofuels herein employ an innovative catalytic process to convert a mixture of methanol and ethanol to a high energy butanol product using an inexpensive, stable copper on hydrotalcite catalyst and moderate temperature, low-pressure process conditions. Existing technology can supply methanol from organic waste via conversion to syngas (carbon monoxide and hydrogen) utilizing commercially available catalysts. Alternatively, the methanol component of PSF can be used to upgrade the ethanol and propanol PSF components to butanol in the same catalytic process.

Successful early testing utilized bench-scale, downflow, fixed-bed test apparatus, adapted for continuous liquid feed with a syringe pump to a vaporization chamber inserted just prior to the fixed-bed reactor containing the catalyst. No carrier gas was used. The vaporized alcohols then passed through the fixed-bed reactor at ~280 C and ~1 bar absolute pressure. The reaction products were condensed in an ice bath. Gases were sampled and vented.

The catalyst is inexpensive (no precious or exotic metals were used) and gave no sign of deterioration over the course of the experiment. Initial shakedown experiments have been conducted to begin optimization of feed composition. High ethanol conversion was achieved at a molar feed ratio of 6.25:1 methanol:ethanol. A high methanol:ethanol feed ratio was used to help maximize ethanol conversion. The catalyst requires a brief break-in period before reaching steady state production of butanol product. A recent test run gave results shown in Table 3:

TABLE 3

Sample Butanol Production Run in Bench-scale Test Rig (wt %)

|  | FEED (liquid) | PRODUCT (liquid) | PRODUCT (gas) |
|---|---|---|---|
| Methanol | 81.3 | 55.44 | 0 |
| Ethanol | 18.7 | 1.32 | 0 |
| Propanol | 0 | 3.08 | 0 |
| Butanol | 0 | 15.95 | 0 |
| Other | 0 | 1.30 | 1.70 |
| $H_2$ | 0 | 0 | 3.48 |
| CO | 0 | 0 | 4.22 |
| $CO_2$ | 0 | 0 | 13.51 |
| Totals | 100 | 77.09 | 22.91 |

The liquid condensate product accounts about 77 percent of the feed mass, with gases accounting for the remainder. Useful gases, (carbon monoxide, hydrogen, and other fuel/oxygenates), account for about 9.4 percent of the feed mass, while waste gas ($CO_2$) accounts for 13.5 percent of the feed mass.

About 93 percent conversion of feed ethanol was achieved. About 19 kg of butanol plus propanol was obtained per 17.4 kg of ethanol consumed. About one-third of the methanol feed was consumed—the excess would be recovered and recycled in an integrated process. These results are remarkable, especially considering that the process had not yet been optimized.

Figure 5:
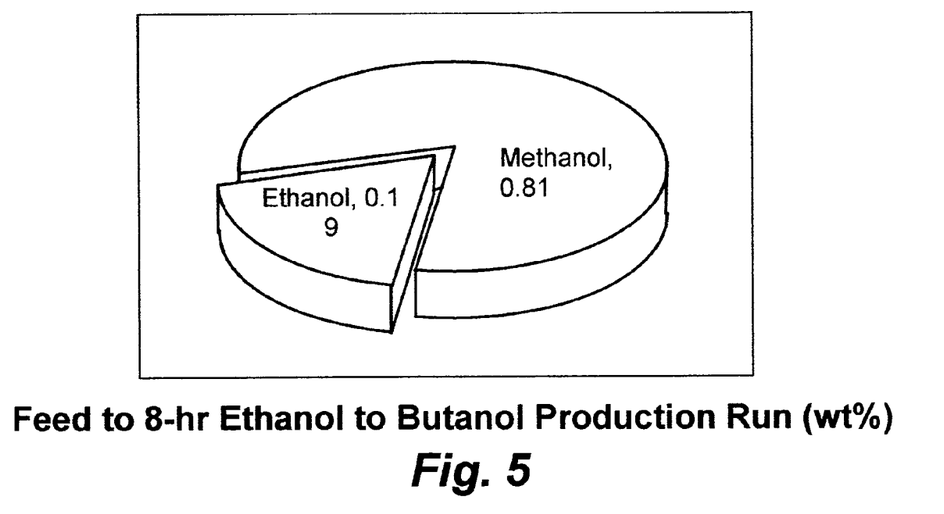
FIG. 5 is a pie chart demonstrating components fed into EtB system.
Figure 6:
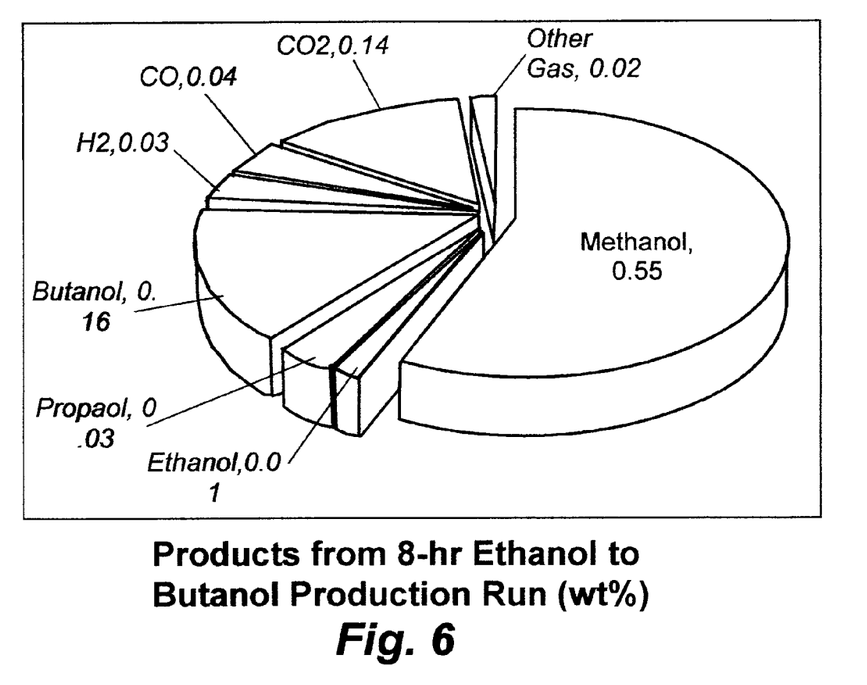
FIG. 6 is a pie chart demonstrating products obtained from EtB system.

A comparison of the feed and the product of the ethanol to butanol (EtB) process is shown in FIGS. 5 and 6.

Using the Reverse Water Gas Shift to Improve Butanol Synthesis Economics

Examining the results in Table 3, it is apparent that some 26 gm of methanol and 17.4 gm of ethanol were consumed in the EtB process of producing 3 gm of propanol and 16 gm of butanol. The fact that so much methanol was consumed in such a system is to be expected, as can be seen by examining the EtB reaction in its ideal form. This can be written:

$$4CH_3OH + C_2H_5OH => C_4H_9OH + 2CO_2 + 6H_2 \quad (6)$$

Equation (6) requires four methanols (with a total molecular weight of 128) to react with one ethanol (weight 46) to produce one butanol (weight 74) plus two carbon dioxide molecules (weight 88) plus 6 hydrogens (weight twelve). The large methanol consumption of such a system would clearly have a negative impact on its economic attractiveness. Indeed, while superior quality fuel would be produced, the system has reduced the total number of fuel carbons from six to four, with the remaining two being expended from the system as carbon dioxide waste.

This problem can be remedied by employing the reverse water gas shift (RWGS) reaction to turn the $CO_2$ into CO. The RWGS reaction can be written as shown in reaction 7:

$$CO_2 + H_2 => CO + H_2O \quad (7)$$

The RWGS reaction has been well-known to chemistry for over a century, but its equilibrium constant at 400° C. is only about 0.1, so only partial yield is ordinarily achieved. Furthermore, unless narrowly catalyzed, alternative more favorable reactions (such as methane formation can occur instead.) However, the inventor developed and demonstrated a closed-loop RWGS system using a catalyst and a membrane separation system that avoided all side reactions and which achieved essentially 100% conversion of $CO_2$ into CO. Combining this system to a methanol synthesis unit employing reaction (4) created a system that produced essentially (>99.99%) pure methanol from hydrogen and $CO_2$. This was the first time anyone had ever created such a system.

By combining the RWGS/methanol unit in series with the EtB reaction (6), the two waste $CO_2$'s and six hydrogens produced by reaction 6 are converted back into methanol, which is recycled, and the net butanol-synthesis system is shown in reaction 8:

$$2CH_3OH + C_2H_5OH => C_4H_9OH + 2H_2O \quad (8)$$

Comparing reaction (8) with reaction (6), the addition of the RWGS/unit to the EtB reaction system allows overall methanol consumption requirements to be cut by a factor of two, and eliminated $CO_2$ waste from the system entirely. Every carbon that entered the system as fuel, left it as fuel—but in a better fuel form than it had going in.

Such an improved "no carbon left behind" RWGS/methanol-augmented EtB system offers clear and unexpected economic advantages over a system lacking such a capability.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

All references cited above are incorporated herein by reference in their entirety.

The words "comprise", "comprises", and "comprising" are to be interpreted inclusively rather than exclusively.

What is claimed is:

1. A method of producing liquid fuel from synthesis gas, the method comprising reacting the gas at pressures between about 500 and about 3000 psi and temperatures between about 200° C. and about 400° C. over a catalyst, wherein the catalyst consists of (i) copper, zinc, and potassium, (ii) copper, zinc, potassium, and cobalt, (iii) copper, zinc, potassium, and manganese, or (iv) copper, zinc, potassium, cobalt, and manganese, on a substrate selected from the group consisting of silica, carbon nanotubes, and aluminum oxide.

2. The method of claim 1, wherein the liquid fuel produced comprises methanol, ethanol, propanol, butanol, hydrocarbons, and/or mixtures thereof.

3. The method of claim 2, wherein the methanol component of the product is removed via distillation to increase the energy content of the remaining fuel.

4. The method of claim 1, wherein the synthesis gas is produced by steam reforming of biomass, corn stover, lignin, hemicellulose, coal, natural gas, landfill gas, and/or trash.

5. The method of claim 1, wherein the synthesis gas is produced using the reverse water gas shift to convert $CO_2$ to CO.

6. The method of claim 1, wherein waste $CO_2$ and hydrogen are converted into CO using reverse water gas shift, and wherein the CO is used as synthesis gas.

7. A method of producing butanol, the method comprising reacting methanol with ethanol, propanol, or mixtures thereof at pressures under 3000 psi and temperatures between about 200° C. and about 400° C. using a catalyst, wherein the catalyst comprises copper on hydrotalcite, and wherein the hydrotalcite is a strongly basic variety with a MgO to $Al_2O_3$ ratio greater than 1:1.

8. The method of claim 7, wherein the methanol is produced on site by reacting synthesis gas on a copper and zinc catalyst at pressures between about 100 psi and about 3000 psi and temperatures between about 200° C. and about 400° C.

9. The method of claim 7, wherein the methanol, ethanol, and/or propanol is produced from synthesis gas derived from of biomass, corn stover, lignin, hemicellulose, coal, natural gas, landfill gas, and/or trash.

10. A method of producing a mixture of butanol, higher alcohols, and hydrocarbons from synthesis gas, the method comprising: (a) reacting the gas at pressures between about 500 and about 3000 psi and temperatures between about 200° C. and about 400° C. over a catalyst, wherein the catalyst consists of (i) copper, zinc, and potassium, (ii) copper, zinc, potassium, and cobalt, (iii) copper, zinc, potassium, and manganese, or (iv) copper, zinc, potassium, cobalt, and manganese, on a substrate selected from the group consisting of silica, carbon nanotubes, and aluminum oxide, to yield a mixture of alcohols and hydrocarbons comprising methanol, ethanol, propanol and butanol, as well as other alcohols and hydrocarbons; and (b) reacting the methanol with the ethanol and/or propanol to produce butanol at pressures under 3000 psi and temperatures between about 200° C. and about 400° C. using a catalyst comprising copper on hydrotalcite.

11. The method of claim 10, wherein the hydrotalcite catalyst employed in step (b) is a basic variety and has a MgO to $Al_2O_3$ ratio greater than 1:1.

12. The method of claim 10, wherein the synthesis gas is produced by steam reformation of biomass, corn stover, lignin, hemicellulose, coal, natural gas, landfill gas, and/or trash.

13. The method of claim 10, wherein the synthesis gas is produced using the reverse water gas shift to convert $CO_2$ to CO.

14. A catalyst consisting of (i) copper, zinc, and potassium, (ii) copper, zinc, potassium, and cobalt, (iii) copper, zinc, potassium, and manganese, or (iv) copper, zinc, potassium, cobalt, and manganese, deposited on a substrate selected from the group consisting of silica, carbon nanotubes, and aluminum oxide.

* * * * *